United States Patent [19]

Beale et al.

[11] 4,243,594

[45] Jan. 6, 1981

[54] PROCESS FOR THE 13-DEOXYGENATION OF A 3,13-DEHYDROXY-GIBBERELLIN

[75] Inventors: Michael H. Beale, Vancouver, Canada; Jake MacMillan, Bristol, England

[73] Assignee: Imperial Chemical Industries Limited, London, England

[21] Appl. No.: 963,743

[22] Filed: Nov. 27, 1978

[51] Int. Cl.$^3$ .................................... C07D 307/00
[52] U.S. Cl. .................................... 260/343.3 G
[58] Field of Search .................................... 260/343.3 G

[56] References Cited

U.S. PATENT DOCUMENTS 4,088,658  5/1978  Robertson .................. 260/343.41

FOREIGN PATENT DOCUMENTS 892777  3/1962  United Kingdom ............ 260/343.3 G

OTHER PUBLICATIONS

Murofushi et al., Agri. Bio. Chem., 41 (6), 1075–1079, 1977.
Cross et al., J.C.S. Part III, 1965, No. 652, pp. 3555–3563.
Beeley et al., J.C.S. Perkin Transactions 1, No. 9, 1976, 1022–1028.
Billingham et al., J.C.S. Chem. Comm., 1977, 344–345.
Barton et al., J.C.S. Perkin I, 1975, 1574–1585.
Fieser & Fieser, Reagents for Organic Synthesis, vol. 2, p. 448.

*Primary Examiner*—Henry R. Jiles
*Assistant Examiner*—Jane T. Fan
*Attorney, Agent, or Firm*—Murray & Whisenhunt

[57] ABSTRACT

13-Hydroxy gibberellins are dehydroxylated by esterifying the 13-hydroxy group with a sulphonic, carboxylic or thiocarboxylic acid or esterifiable derivative thereof and then reducing the 13-ester group with a tri-alkyltin hydride which is a selective reagent so that it is possible to remove a 13-hydroxy group in a gibberellin containing further hydroxy groups and/or lactone bridges. $GA_3$ can be converted to $GA_7$ by this process.

8 Claims, No Drawings

PROCESS FOR THE 13-DEOXYGENATION OF A 3,13-DEHYDROXY-GIBBERELLIN

DESCRIPTION

This invention relates to gibberellins and is particularly concerned with a process for the 13-deoxygenation (also referred to as dehydroxylation) of gibberellins and to new intermediates prepared during the synthesis.

Gibberellins are a well-recognised group of tetracyclic compounds which have been found to be of use as plant growth hormones. Many gibberellins are found to occur naturally in plants and other gibberellins can be produced by fermentation methods. Over fifty gibberellins have now been reported in the literature. Gibberellins are based on the tetracyclic ring structure of formula I which shows the ring numbering.

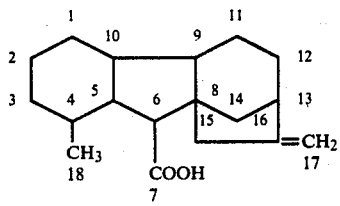

One gibberellin which can be readily obtained by fermentation methods is the gibberellin known as $GA_3$ of formula II

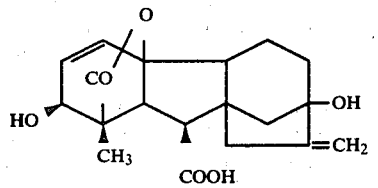

$GA_3$, like many other gibberellins, has a 13-hydroxy group. This hydroxy group is a tertiary hydroxy group located at one of the bridge heads in the molecule. In the gibberellin field, it is often found that removal of a 13-hydroxy group, or replacement of the 13-hydroxy group by another substituent can have advantageous effects on the overall properties of the compound, for example, the 13-deoxy analogue of $GA_3$ which is $GA_7$, is known to exhibit advantageous properties not shown by $GA_3$.

Consequently, it would be advantageous to have available a process for the 13-deoxygenation of 13-hydroxy gibberellins so that they could be converted, semi-synthetically, into gibberellins which were either unsubstituted at position-13 or substituted by another group.

Conventional methods of dehydroxylating organic compounds, e.g. steroids, are not satisfactory for use with gibberellins because of the other sensitive sites in the gibberellin molecule which would be adversely affected during the deoxygenation reaction. For example, many gibberellins have one or more further hydroxy groups in the molecule which it is desired to retain and which would be removed together with the 13-hydroxy group during the relatively severe reaction conditions that are necessary to remove this tertiary hydroxy group. $GA_3$, mentioned above, is one such gibberellin and in addition, $GA_3$ includes a 4,10-lactone bridge which is also sensitive to many reaction conditions, tending to migrate to the 2-4 position easily.

It is also necessary to select deoxygenation conditions which will not adversely affect the carboxy group present at the 6-position in all gibberellins or the methylene group substituted at position-16.

We have now found that 13-deoxygenation of 13-hydroxy gibberellins can be achieved satisfactorily by esterifying the 13-hydroxy group in a 13-hydroxy gibberellin with a sulphonic, carboxylic or thiocarboxylic acid and reducing the resulting ester with a trialkyltin hydride.

The esterification of the 13-hydroxy group is preferably carried out using an organosulphonyl chloride such as an alkylsulphonyl chloride, e.g. methyl- or ethylsulphonyl chloride or an arylsulphonyl chloride such as phenyl- or p-tolylsulphonyl chloride. Instead of using the sulphonyl chloride, other known methods of esterifying a tertiary hydroxy group can be used. As an alternative to esterifying the 13-hydroxy group with an organosulphonyl group, it can be esterified with a carboxylic or thiocarboxylic acid, e.g. an aromatic acid such as benzoic or thiobenzoic acid, again preferably used in the form of its acid chloride. When the esterification is carried out using the acid chloride, it will normally be carried out in the presence of a hydrogen halide acceptor, typically a secondary or tertiary amine such as triethylamine, pyridine or piperidine and using a solvent such as methylene chloride, pyridine etc. To optimise the reaction, the esterification is normally carried out with equimolar amounts of the sulphonyl chloride and of the hydrogen chloride acceptor.

During the esterification of the 13-hydroxy group with the acid chloride it is inevitable that the carboxy group at the 6-position will be converted to the acid chloride. This conversion can be monitored by the acidity of the sulphonylated product and, before proceeding to the next step of the synthesis, it is usually desirable to reinstate the 6-carboxy group by treatment with alkali, for example, by treatment with sodium carbonate or sodium bicarbonate in aqueous acetone.

The final step in the synthesis involves the reduction of the sulphonyl ester group at position-13 with the trialkyltin hydride reagent. This reagent, which is preferably used in the freshly prepared state, and can be prepared by treating the trialkyltin chloride with lithium aluminium hydride, has been found to react in a very specific manner with the 13-sulphonyloxy ester grouping on gibberellins to remove the oxygenated substituent completely at position-13 leaving hydrogen.

Availability points to the use of tri-n-butyltin hydride as the reagent of choice. This reagent operates by a free radical mechanism and it is therefore important to have present in the reaction mixture a source of free radicals. For this purpose, we have found α-azo-isobutyronitrile to be particularly suitable. It is only necessary to have the free radical initiator present in catalytic quantities.

Under our experimental conditions, we have found that it is possible to bring about substantially complete conversion of the 13-sulphonyloxy ester grouping in gibberellins to the 13-unsubstituted compound by refluxing the reaction mixture in an organic diluent such as benzene, toluene or other inert solvent for up to about 48 hours.

As mentioned above, one of the main advantages of the present process is its selectivity to the 13-deoxygenation of gibberellins containing sensitive substituents in other parts of the molecule. Where the gibberellin contains potentially susceptible substituents in other parts of the molecule, for example, other hydroxy groups which it is desired to retain, it is necessary to protect those other hydroxy groups during the 13-deoxygenation. This can be done by conventional methods and we have found in the GA$_3$ series, for example, that the 3-hydroxy group can be satisfactorily protected by acetylation. However, acetylation is only one method of protecting the hydroxy group and other protecting groups, conventionally used in gibberellin or steroid chemistry e.g. ether groups or ester groups, can be used.

The advantage of using acylation in the GA$_3$ series is that the acyl group can be removed after the 13-deoxygenation by treating the 13-dehydroxylated product with an alcoholic alkali, for example sodium or potassium carbonate, the avoidance of an aqueous system thereby ensuring that the lactone bridge is not opened or isomerised.

While the present process is generally applicable to the 13-deoxygenation of any gibberellin, it is particularly designed for use with gibberellins containing additional hydroxy groups in the molecule which it is desired to retain. These additional hydroxy groups will normally be secondary hydroxy groups and our deoxygenation is of particular value with those gibberellins containing allylic secondary hydroxy groups such as in the GA$_3$ series.

Our synthesis is particularly valuable for the conversion of GA$_3$ to GA$_7$ since it is possible to protect the 3-hydroxy group initially by acetylation, to esterify the 13-hydroxy group, preferably with methyl sulphonyl chloride to form a 3-acetoxy 13-mesyloxy acid chloride derivative of the GA$_3$, to reconvert the acid chloride group back to the carboxylic acid group, to split off the mesyloxy group by treatment of the ester with tri-n-butyltin hydride and finally to remove the acetyl protecting group at the 3-hydroxy. In this sequence of reactions, each step can be carried out in a selective manner so that, for example, esterification of the 3-hydroxy and then the 13-hydroxy groups followed by demesylation and removal of the 3-hydroxy protecting group can all be carried out under conditions which do not open or isomerise the lactone ring.

This reaction has been developed primarily for the conversion of GA$_3$ to GA$_7$, since, although GA$_7$ can be prepared directly by fermentation, it is always produced in association with GA$_4$ (its analogue having a saturated A ring) and it is very difficult to separate the mixture of GA$_7$ and GA$_4$. GA$_3$ can be readily produced by fermentation and our procedure provides a selective semi-synthetic route for producing GA$_7$ free from GA$_4$.

However, our technique is also applicable to the 13-deoxygenation of other 13-hydroxy gibberellins and can be used, for example, for the conversion of GA$_1$ to GA$_4$, or for the conversion of GA$_{20}$ to GA$_9$, or for the conversion of GA$_8$ to GA$_{34}$. All of these starting gibberellins have a 13-hydroxy group and, in addition, a 4,10-lactone bridge and, for GA$_1$, one secondary and, for GA$_8$, two secondary hydroxy groups, all of which can be retained in their original form after the 13-deoxygenation.

The sulphonic acid, carboxylic acid and thiocarboxylic acid esters of the 13-hydroxy gibberellins, produced as intermediates in the 13-deoxygenation process of the invention are new compounds and form a further aspect of the present invention. More particularly, the present invention provides gibberellins containing a 13-sulphonyloxy, carbonyloxy or thiocarbonyloxy group and, in addition, a protected secondary hydroxy group and/or a 4,10-lactone bridge. It is convenient that the protected hydroxy group be in the A ring, e.g. in the 3-position and that the A ring be unsaturated, particularly in a manner such that the secondary hydroxy group is an allylic hydroxy group. The secondary hydroxy group may be protected by any of the protecting groups customarily used in gibberellin or steroid chemistry, for example as a removable ether or ester group. It is preferred that such protecting groups be organocarbonyl groups such as lower alkanoyloxy groups containing 1 to 4 carbon atoms in the alkyl residue or aroyl groups, e.g. benzoyl. When the hydroxy group is etherified, it may be etherified for example as a tetrahydropyranyl ether.

More particularly, the present invention provides a new derivative of GA$_3$ of the formula

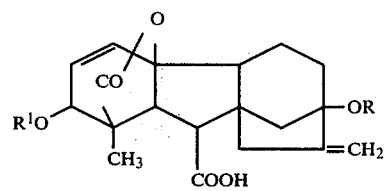

where OR is the sulphonyloxy, carbonyloxy or thiocarbonyloxy group and OR$^1$ is the protected hydroxy group.

The present invention also specifically provides 13-sulphonyloxy, carbonyloxy and thiocarbonyloxy derivatives of GA$_1$, GA$_{20}$, and GA$_8$ where any additional secondary hydroxy groups in the molecule are protected.

The corresponding acid chlorides, which can be obtained during esterification of the 13-hydroxy gibberellin with an acid chloride, are also new compounds and form part of this invention.

Our studies have been carried out on naturally occurring gibberellins or gibberellins obtained by fermentation. In all these compounds, the substituents at the 3,4 and 6-positions are in the β-position and the configuration of these substituents is retained after the deoxygenation of the invention. Consequently, the deoxygenation process can be carried out without influencing the configuration of the gibberellins.

The following Example is given to illustrate the invention.

EXAMPLE

This Example describes the conversion of GA$_3$ to GA$_7$ by protecting the 3β-hydroxy group by acetylation, mesylating the 13-hydroxy group with mesyl chloride, reconverting the acid chloride group to the carboxylic acid group, removing the mesyloxy group by reaction with tri-n-butyltin hydride and finally removing the protecting acetoxy group at the 3β-hydroxy by treatment with methanolic potassium carbonate.

(a) 3β-acetoxy GA$_3$

GA$_3$ (1 g) was treated with 6.4 ml of acetic anhydride in pyridine (12 ml) overnight. The reaction mixture was poured into water, acidified and extracted with ethyl acetate. The product, obtained on removal of the ethyl acetate, was fractionally crystallised from acetone petroleum ether to give 825 mg of pure 3β-acetoxy GA$_3$.

(b) 3β-acetoxy-13-mesyloxy GA₃

The crystalline product from step (a) (825 mg) was dissolved in 10 ml pyridine and 1 ml triethylamine and 1 ml methanesulphonyl chloride was added. The mixture was stirred for 5 hours and then poured into water. The aqueous mixture was acidified and extracted with ethyl acetate. At this stage the product was found to consist mainly of acetoxymesyloxy GA₃ in the carboxylic acid chloride form. The product was dissolved in 40 ml acetone to which 20 ml saturated sodium hydrogen carbonate and 20 ml water were added. This mixture was stirred for 15 hours at about 20° C. and then the acetone removed in vacuo. The aqueous residue was then acidified with hydrochloric acid and extracted with ethyl acetate. The organic residue was then absorbed onto silica and chromatographed on a silica column (120 g) (30×3 cm) made up in petroleum ether.

The column was then eluted initially with petroleum ether and a 250 ml fraction collected. The column was then eluted with successive 250 ml fractions of petroleum ether containing increasing quantities of ethyl acetate as follows:

| Proportion of ethyl acetate in percent by volume | Fraction number |
| --- | --- |
| 0 | 1 |
| 5 | 2 |
| 10 | 3 |
| 20 | 4 |
| 100 | 5,6 |

Fractions 1–4 were rejected. Fractions 5 and 6 were found to contain 3-acetoxy-13-mesyloxy GA₃ (901 mg).

The identity of the product was confirmed by mass spectrometry and NMR, NMR giving a 3 proton singlet peak at δ3 confirming the presence of the 13-methanesulphonyl group and another 3 proton singlet at δ2.05 indicating the presence of the 3-acetoxy group. Corresponding peaks were also found for the carboxylic acid chloride analogue of this compound which was also examined by NMR.

(c) 3β-acetoxy-13-deoxy GA₃

The di-ester recovered in fractions 5 and 6 above (901 mg) was dissolved in 25 ml benzene and 20 mg α-azo-isobutyronitrile and 2 ml of freshly prepared tri-n-butyltin hydride added. The mixture was refluxed under nitrogen for 24 hours after which time it was found that approximately 60% of the gibberellin had been dehydroxylated. A further 500 μl of tri-n-butyltin hydride and 10 mg of α-azo-isobutyronitrile were then added and the mixture heated again under nitrogen for a further 15 hours.

TLC examination after this second period of heating indicated that the reaction was now complete. The benzene was removed in vacuo and the product absorbed, from an acetone solution, onto silica and chromatographed on a column of silica (120 g, 30×3 cm) made up in petroleum ether. The column was eluted with petroleum ether containing increasing quantities of ethyl acetate—250 ml fractions were collected as follows:

| Proportion of ethyl acetate in percent by volume | Fraction number |
| --- | --- |
| 0 | 1 |
| 5 | 2 |
| 10 | 3 |
| 100 | 4,5 |

Fractions 1–3 contained residues from tri-n-butyltin hydride and were discarded. Fractions 4 and 5 yielded an oil (850 mg) containing 3-acetoxy-13-deoxy-GA₃ together with some tin containing residues.

(d) GA₇

The product from step (c) above (850 mg) was taken up in 20 ml methanol and 425 mg potassium carbonate were added. This mixture was stirred at about 20° C. for 15 hours and then 4 g of an ion exchange resin in the acid form (Amberlite IR-120, H+) was added to remove the potassium carbonate. After 15 minutes this mixture was filtered and the organic solvent removed. The residue was partitioned between ethyl acetate and sodium hydrogen carbonate solution. GA₇ (419 mg) was recovered from the bicarbonate phase and shown to be identical (TLC and NMR) to an authentic sample.

We claim:

1. A process for the 13-deoxygenation of a 3,13-dihydroxy-gibberellin which comprises esterifying the 13-hydroxy group in a 3,13-dihydroxy gibberellin by reaction with a sulphonic acid or a carboxylic acid or a thiocarboxylic acid or an esterifiable derivative of one of said acids to form a 13-ester and then treating the 13-ester with a trialkyltin hydride in the presence of a free-radical initiator to reduce the 13-ester and form a 13-deoxygenated gibberellin, provided that when the esterifiable derivative is the acid chloride, the 6-carboxy group of the 3,13-dihydroxy gibberellin, which is converted to the corresponding acid chloride, is reinstated by treatment with an alkali, and further provided that the 3-hydroxy group and any further hydroxy group in the gibberellin is protected by a protecting group before esterification of the 13-hydroxy group, and each protecting group is removed after the 13-deoxygenation.

2. A process according to claim 1 wherein the 3,13-dihydroxy gibberellin is reacted with an alkylsulphonyl chloride or an aryl sulphonyl chloride or benzoic acid chloride.

3. A process according to claim 1 or 2 wherein the trialkyltin hydride is tri-n-butyltin hydride.

4. A process according to claim 3 wherein the 13-ester is refluxed in an inert organic diluent in the presence of α-azo-isobutyronitrile.

5. A process according to claim 1 wherein the 3-hydroxy group is an allylic hydroxy group.

6. A process according to claim 1 wherein the 3,13-dihydroxy gibberellin has 4,10-lactone bridge.

7. A process according to claim 1 wherein the 3,13-dihydroxy gibberellin is GA₃ and the 13-deoxygenated gibberellin is GA₇.

8. A process according to claim 9 wherein GA₃ is treated with an acetylating agent to form a 3β-acetoxy-GA₃, the 3β-acetoxy GA₃ is treated with mesyl chloride to form 3β-acetoxy-13-mesyloxy-GA₃, the 3β-acetoxy-13-mesyloxy-GA₃ is treated with tri-n-butyltin hydride in the presence of α-azo-isobutyronitrile to form 3β-acetoxy-13-deoxy GA₃ and the 3β-acetoxy-13-deoxy-GA₃ is treated with alkali to deacetylate the 3β-acetoxy-13-deoxy GA₃ to form GA₇.

* * * * *

UNITED STATES PATENT OFFICE
CERTIFICATE OF CORRECTION

Patent No. 4,243,594   Dated January 6, 1981

Inventor(s) Michael Henry BEALE, ET AL

It is certified that error appears in the above-identified patent and that said Letters Patent are hereby corrected as shown below:

In the heading: second line of paragraph [30] should read:

-- Jul. 18, 1978 [GB] United Kingdom.............30173/78 --

Signed and Sealed this

Thirty-first Day of March 1981

[SEAL]

Attest:

RENE D. TEGTMEYER

Attesting Officer   Acting Commissioner of Patents and Trademarks